United States Patent
Liou et al.

(10) Patent No.: US 9,410,902 B1
(45) Date of Patent: Aug. 9, 2016

(54) OVERLAY MEASUREMENT METHOD

(71) Applicant: UNITED MICROELECTRONICS CORP., Hsin-Chu (TW)

(72) Inventors: En-Chiuan Liou, Tainan (TW); Yi-Jing Wang, Tainan (TW)

(73) Assignee: UNITED MICROELECTRONICS CORP., Hsin-Chu (TW)

( * ) Notice: Subject to any disclaimer, the term of this patent is extended or adjusted under 35 U.S.C. 154(b) by 0 days.

(21) Appl. No.: 14/703,890

(22) Filed: May 5, 2015

(51) Int. Cl.
*G01B 11/14* (2006.01)
*G01N 21/95* (2006.01)
*G01B 11/27* (2006.01)
*G01N 21/88* (2006.01)

(52) U.S. Cl.
CPC ............ *G01N 21/9501* (2013.01); *G01B 11/27* (2013.01); *G01N 21/8806* (2013.01); *G01N 2021/8825* (2013.01)

(58) Field of Classification Search
CPC ........... G06K 9/00; G06K 9/36; G01N 21/95; G01N 21/27; G01N 21/88
See application file for complete search history.

(56) References Cited

U.S. PATENT DOCUMENTS

| | | |
|---|---|---|
| 5,695,897 A | 12/1997 | Mitome |
| 5,808,742 A | 9/1998 | Everett |
| 5,837,404 A | 11/1998 | Lu |
| 6,071,656 A | 6/2000 | Lin |
| 7,230,705 B1 | 6/2007 | Yang |
| 7,427,459 B2 | 9/2008 | Chen |
| 8,043,928 B2 | 10/2011 | Sogawa |
| 8,072,615 B2 | 12/2011 | Musa |
| 8,779,556 B2 | 7/2014 | Chen |
| RE45,245 E | 11/2014 | Ghinovker |
| 8,908,175 B1 | 12/2014 | Kandel |
| 8,913,237 B2 | 12/2014 | Levinski |
| 8,948,495 B2 | 2/2015 | Marcuccilli |
| 2008/0095407 A1* | 4/2008 | Stewart ............... G06K 9/3216 382/106 |
| 2011/0115057 A1 | 5/2011 | Harn |

* cited by examiner

*Primary Examiner* — Tarifur Chowdhury
*Assistant Examiner* — Jamil Ahmed
(74) *Attorney, Agent, or Firm* — Winston Hsu; Scott Margo

(57) ABSTRACT

An overlay measurement method includes providing three predetermined patterns, including a first predetermined pattern, a second predetermined pattern and a third predetermined pattern. An inspection process is then performed on said three predetermined patterns, to obtain three image points, including a first image point, a second image point and a third image point respectively. Next, a defining process is performed to define a default position, and a calculating process is performed to obtain a real offset value $x=(p-q)*(c-a)/(a-b)+p$.

16 Claims, 3 Drawing Sheets

OVERLAY MEASUREMENT METHOD

BACKGROUND OF THE INVENTION

1. Field of the Invention

The present invention relates generally to the field of semiconductor manufacturing processes, and more particularly to a method of correcting overlay error in photolithographic processes.

2. Description of the Prior Art

Photolithography is an essential step in semiconductor manufacturing processes, through which the pattern of integrated circuits may be transferred from photomasks to semiconductor chips. Generally, a design layout of integrated circuit provided by an IC design house may be divided into several layers of design layouts after it is received by the semiconductor manufacturing company. These design layouts may be then fabricated on the corresponding transparent plates to thereby form photomasks with desired layouts. The layout of each of the photomasks may be respectively transferred to a photoresist layer on the chip through suitable photolithographic process. Afterwards, other suitable processes, such as etching, deposition, doping and so forth may be carried out in order to obtain required semiconductor devices.

Recently, the measurement of the overlay between two or more successive layers becomes more and more important along with the continuous miniaturization in integrated circuits. For instance, through vias and contacts are often used to electrically connect interconnections in different layers to one another. Because the interconnections, the through vias and/or the contacts are generally disposed in different layers, a process of overlay measurement needs to be carried out during each of the corresponding photolithographic processes so as to assure the minimum shift between successive layers.

However, the current overlay measurement still has some drawbacks. For example, due to measurement deviation, the measured values of relative positions between successive layers often fail to reflect their real positions. Therefore, the measurement results often include overlay error.

Accordingly, there is a need to provide an improved method of correcting overlay error so as to increase the accuracy of the measurement results.

SUMMARY OF THE INVENTION

The present invention provides an overlay measurement method, comprising: firstly, three predetermined patterns are provided, including a first predetermined pattern, a second predetermined pattern and a third predetermined pattern. An inspection process is then performed on said three predetermined patterns to obtain three image points, including a first image point, a second image point and a third image point respectively. Next, a defining process is performed to define a default position, and a calculating process is performed to obtain a real offset value $x=(p-q)*(c-a)/(a-b)+p$, wherein: p is the distance between the first predetermined pattern and the third predetermined pattern; q is the distance between the second predetermined pattern and the third predetermined pattern; a is the offset value between the default position and the first image point; b is the offset value between the default position and the second image point; and c is the offset value between the default position and the third image point. In addition, said inspection process, said defining process and said calculating process are performed through a computer system.

The present invention provides an overlay measurement method, comprising: firstly, a wafer is loaded into an apparatus, and three predetermined patterns are defined on the wafer, including a first predetermined pattern, a second predetermined pattern and a third predetermined pattern. An inspection process is then performed on said three predetermined patterns to obtain three image points, including a first image point, a second image point and a third image point respectively. Next, a defining process is performed to define a default position, and a calculating process is performed to obtain a real offset value $x=(p-q)*(c-a)/(a-b)+p$, wherein: p is the distance between the first predetermined pattern and the third predetermined pattern; q is the distance between the second predetermined pattern and the third predetermined pattern; a is the offset value between the default position and the first image point; b is the offset value between the default position and the second image point; and c is the offset value between the default position and the third image point. In addition, said inspection process, said defining process and said calculating process are performed through a computer system.

In summary, the present invention provides a method for correcting overlay error. First of all, three predetermined patterns are disposed on the wafer, and a pattern is also be defined on the wafer. Afterwards, an inspection process is performed, to obtain three image points: a first image point, a second image point and a third image point respectively. Thereafter, a calculating process is performed, so as to calculate the real offset value between the predetermined pattern and the default position. Therefore, the real offset can be corrected in the following processes. Hence, the detection error caused by the difference in the refractive indexes may be eliminated. Accordingly, the accuracy of the overlay measurement is enhanced.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
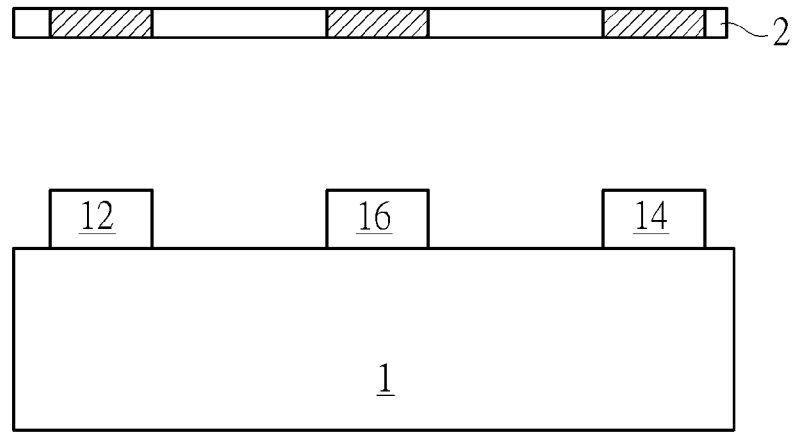
FIGS. 1-2 show the cross section diagrams of a wafer of the present invention.

In the following description, numerous specific details are given to provide a thorough understanding of the invention. It will, however, be apparent to one skilled in the art (note: of ordinary skill in the art) that the invention may be practiced without these specific details. Furthermore, some well-known system configurations and process steps are not disclosed in detail, as these should be well-known to those skilled in the art.

Likewise, the drawings showing embodiments of the apparatus are not to scale and some dimensions are exaggerated for clarity of presentation. Also, where multiple embodiments are disclosed and described as having some features in common, like or similar features will usually be described with same reference numerals for ease of illustration and description thereof.

Please refer to FIG. 1, which shows a cross section diagram of a wafer of the present invention. In the present invention, the wafer 1 is used to be loaded into an apparatus, so as to calculate a real offset value x, and thereby correcting the overlay error. The method is described in the flowing paragraph:

First, a photomask 2 is provided, and at least three patterns are defined and separated on the photomask 2. Next, through suitable processes, such as photolithography, etching, deposition and planarization, the patterns on the photomask 2 are transferred from the photomask 2 to the wafer 1, so as to form at least three patterns on the wafer 1, labeled as: a first predetermined pattern 12, a second predetermined pattern 14 and a third predetermined pattern 16 respectively. Usually, the first predetermined pattern 12, the second predetermined pattern 14 and the third predetermined pattern 16 can be formed on the scribe line of the wafer, but not limited thereto, it can also be the gate structure, the contact structure or the interconnect structure.

Figure 2:
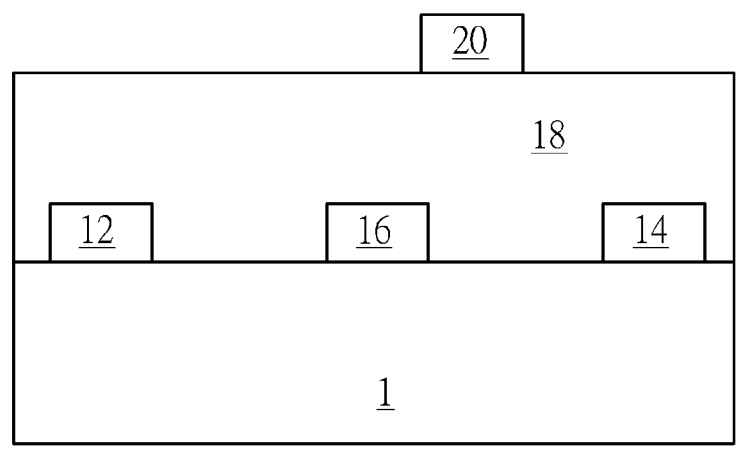

Afterwards, as shown in FIG. 2, a dielectric layer 18 is then formed on the wafer, covering the first predetermined pattern 12, the second predetermined pattern 14 and the third predetermined pattern 16, and a pattern 20 such as a photoresist layer is formed on the dielectric layer 18.

In the present invention, the distance between the first predetermined pattern 12 and the third predetermined pattern 16 is p; the distance between the second predetermined pattern 14 and the third predetermined pattern 16 is q. It is noteworthy that distance p and/or q are decided by measuring the patterns on the wafer 1 or measuring the photomask 2. More precisely, by a suitable photolithography process, the distance between each pattern on the photomask 2 is transferred to the wafer, and the distance p and/or q can be measured through an inspection process (not shown) after the first predetermined pattern 12, the second predetermined pattern 14 and the third predetermined pattern 16 are formed on the wafer 1. But in order to avoid some errors caused by the difference in the refractive index of dielectric layer, the inspection process is preferably performed before the dielectric layer 18 is formed. In another case, the distance p/q can also be decided by measuring the layout pattern or measuring the pattern on the photomask 2. Usually, the patterns on the wafer are same as the patterns on the photomask after scaling down. Therefore, after measuring the distances on the photomask, and the distances are divided to a weight (the scale), the distances p/q on the wafer 1 can be obtained.

Besides, the first predetermined pattern 12, the second predetermined pattern 14 and the third predetermined pattern 16 are formed on a plane and separated from each other. In other words, the first predetermined pattern 12, the second predetermined pattern 14 and the third predetermined pattern 16 can be formed in a same level of the wafer 1. Preferably, the distance p and the distance q are smaller than 20 μm, but not limited thereto. In addition, in one embodiment of the present invention, the first predetermined pattern 12, the second predetermined pattern 14 and the third predetermined pattern 16 are formed and arranged along a straight line, such as the cross section shown in FIG. 1, but the present invention is not limited thereto, the first predetermined pattern 12, the second predetermined pattern 14 and the third predetermined pattern 16 may be separated from each other, and not arranged along a line. However, the distance p and q can still be decided by measuring each pattern on the photomask 2.

Figure 3:
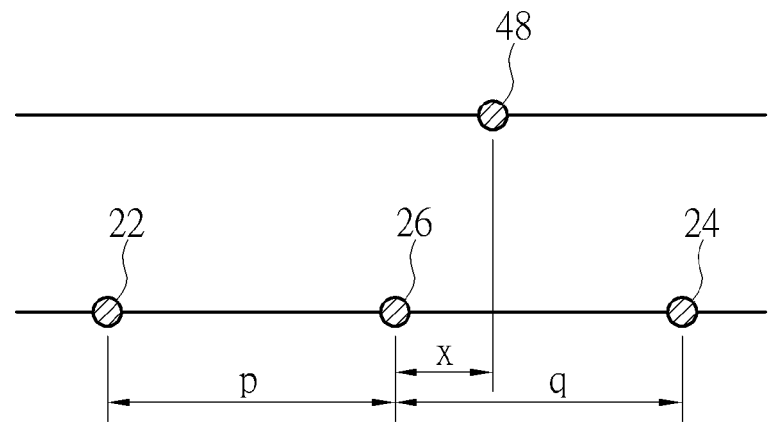
FIGS. 3-4 show the schematic diagrams including the central position of each patterns.

In this case, in order to simplify the description, please refer to FIG. 3, which shows the schematic diagram including the central position of each patterns. As shown in FIG. 3, a first point 22, a second point 24 and a third point 26 are labeled in FIG. 3, wherein the first point 22 is the central point of the first predetermined pattern 12, the second point 24 is the central point of the second predetermined pattern 14, and the third point 26 is the central point of the third predetermined pattern 16. Besides, a default position 48 is the central point of the pattern 20.

Figure 4:
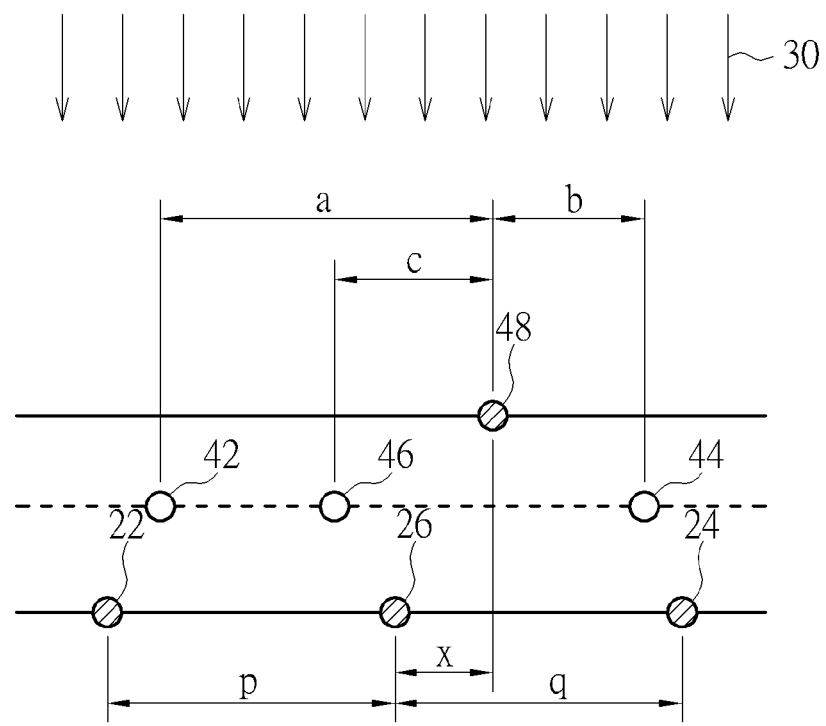

Next, as shown in FIG. 4, an inspection process 30 is performed on the first point 22, the second point 24 and the third point 26. The inspection process 30 such as a diffraction based overlay (DBO) step or an image based overlay (IBO) step, to measure the first point 22, the second point 24 and the third point 26 respectively, and to thereby generate the overlay mark information. The overlay mark information may be an image file including a first image point 42, a second image point 44 and a third image point 46 respectively, wherein the first image point 44 is the pattern or the position corresponding to the first point 22 after the inspection process 30 is performed. Similarly, the second image point 44 corresponds to the second point 24; and the third image point 46 corresponds to the third point 26.

Because of inherent detection error in detection tools, such as error induced by the difference in the refractive index of dielectric layers, the measurement result is often deviated from the real situation. Therefore, each image point may deviate from each corresponding predetermined pattern.

In this embodiment, the default position 48 and the first point 22, the second point 24 and the third point 26 are disposed on different levels. Preferably, when viewed in cross section views (such as FIG. 3), the default position 48 is disposed above the first point 22, the second point 24 and the third point 26. It is noteworthy that the pattern 20 is formed before the wafer 1 is loaded into the apparatus, the pattern 20 (the default position 48) can also be formed on the scribe line of the wafer, which can be used as the origin point in the following overlay correcting steps. It will be described in more detail in the following paragraphs.

In order to obtain the real offset between the predetermined pattern and the default position 48, a calculating process is needed to be performed so as to correct the offset error between the predetermined pattern and the default position. In one embodiment, take the third point 26 as a reference point, and the distance p and q are known by measuring the layout pattern or measuring the photomask 2. After the inspection process 30, three image points: the first image point 42, the second image point 44 and the third image point 46 are obtained. Next, the position of the default position 48 is defined. Afterwards, another measuring process is performed, so as to measure the offset value between the default position 48 and the first image point 42, the second image point 44 and the third image point 46. More precisely, the offset value between the default position 48 and the first image point 42 is labeled as "a"; the offset value between the default position 48 and the second image point 44 is labeled as "b"; and the offset value between the default position 48 and the third image point 46 is labeled as "c". In addition, since the third point 26 is used as the reference, a real offset value (the distance between the third point 26 and the default position 48) is labeled as "x".

Figure 5:
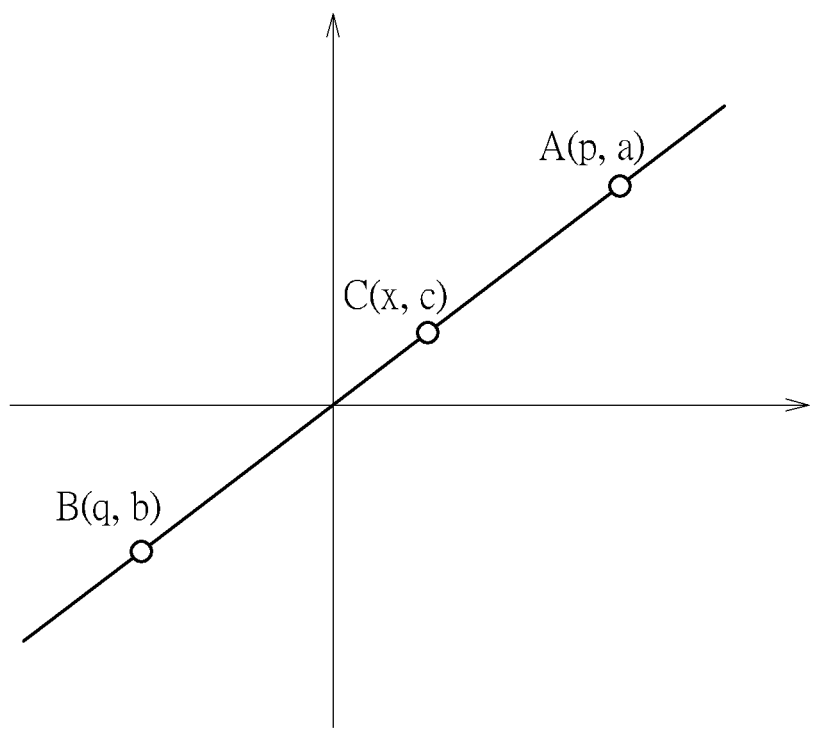
FIG. 5 is a coordinate axis, wherein the distances p, q and x are labeled on the horizontal axis of the coordinate axis, and the measurement overlay offset a, b and c are labeled on the vertical axis of the coordinate axis.

Next, as shown in FIG. 5, FIG. 5 is a coordinate axis, wherein the distances p, q and x are labeled on the horizontal axis of the coordinate axis, and the measurement overlay offset a, b and c are labeled on the vertical axis of the coordinate axis. Therefore, three points A, B and C are obtained, wherein the coordinates of point A is (p, a); the coordinates of point B is (q, b), and the coordinates of point C is (x, c), wherein:

p is the distance between the first point 22 and the third point 26;

q is the distance between the second point 24 and the third point 26;

a is the offset value between the default position 48 and the first image point 42;

b is the offset value between the default position 48 and the second image point 44;

c is the offset value between the default position 48 and the third image point 46;

x is the real offset value between the third point 26 and the default position 48.

Since the points A, B and C are arranged along a straight line, they satisfy the linear relationship. In other words, since the slope of line A-B=the slope of line A-C, therefore:

$$(x-p)/(c-a) = \qquad \text{equation (1)}$$
$$(p-q)/(a-b) \to x = (p-q)*(c-a)/(a-b) + p$$

In the case mentioned above, point C is disposed between point A and point B, but in another case, if point C is disposed on the extending portion of line A-B, the following relationship is satisfied:

$$(x-q)/(c-b) = \qquad \text{equation (2)?}$$
$$(p-q)/(a-b) \to x = (p-q)*(c-b)/((a-b) + q$$

It is noteworthy that said inspection process 30, said defining process and said calculating process are performed through a computer system. In one aspect, a predetermined pattern for an overlay metrology measurement of a semiconductor wafer may be selected. The overlay sites of a selected predetermined pattern of the semiconductor wafer may be detected using any suitable inspection process and any suitable inspection system. For example, the inspection results may be acquired using a bright-field (BF) inspection system, dark-field (DF) inspection system or an electron beam inspection system. Moreover, the results of the inspection by the inspection system may include overlay site locations, sizes, images of the sites, or any other output generated by an inspection system. Moreover, the overlay sites of the selected predetermined pattern of the semiconductor wafer may be detected using a virtual inspection (VI) process.

In one embodiment, a pattern of interest (POI) may be identified by a user. For example, a POI that is selected by a user may be identified on the semiconductor wafer by utilizing data from electronic design automation (EDA) tools, design based binning (DBB), and other knowledge. For example, the POI may be selected as a pattern that forms part of a critical path or is located at or near a critical path on the same layer as the POI or on another layer of the wafer. In addition, the design data may be searched for one or more POIs in any suitable manner.

In summary, the present invention provides a method for correcting overlay error. First of all, three predetermined patterns are disposed on the wafer, and a pattern is also be defined on the wafer. Afterwards, an inspection process is performed, to obtain three image points: a first image point, a second image point and a third image point respectively. Thereafter, a calculating process is performed, so as to calculate the real offset value between the predetermined pattern and the default position (the pattern 20 disposed on the upper level). Therefore, the real offset can be corrected in the following processes. Hence, the detection error caused by the difference in the refractive indexes may be eliminated. Accordingly, the accuracy of the overlay measurement is enhanced.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A overlay measurement method, comprising:

providing three predetermined patterns: a first predetermined pattern, a second predetermined pattern and a third predetermined pattern;

performing an inspection process on said three predetermined patterns, to obtain three image points: a first image point, a second image point and a third image point respectively;

performing a defining process to define a default position; and performing a calculating process to obtain a real offset value x=(p−q)*(c−a)/(a−b)+p, wherein:

p is the distance between the first predetermined pattern and the third predetermined pattern;

q is the distance between the second predetermined pattern and the third predetermined pattern;

a is the offset value between the default position and the first image point;

b is the offset value between the default position and the second image point; and c is the offset value between the default position and the third image point;

wherein said inspection process, said defining process and said calculating process are performed through a computer system.

2. The method of claim 1, wherein the distance p is smaller than 20 um.

3. The method of claim 1, wherein the distance q is smaller than 20 um.

4. The method of claim 1, wherein the first predetermined pattern, the second predetermined pattern and the third predetermined pattern are disposed on a same layer of a wafer.

5. The method of claim 4, wherein the default position is disposed on another layer different the layer having the first predetermined pattern.

6. The method of claim 1, wherein the real offset value x further satisfies the relationship: x=(p−q)*(c−b)/(a−b)+q.

7. The method of claim 1, wherein the inspection process comprises a virtual inspection technique.

8. The method of claim 1, wherein the inspection process includes one of the group including a bright-field inspection technique, a dark-field inspection technique, and an electron beam inspection technique.

9. A overlay measurement method, comprising:

loading a wafer into an apparatus, wherein at least three predetermined patterns are defined on the wafer, including: a first predetermined pattern, a second predetermined pattern and a third predetermined pattern, and the wafer further comprises a default position defined thereon;

performing an inspection process on said three predetermined patterns on the wafer, so as to obtain three image points: a first image point, a second image point and a third image point respectively;

performing a calculating process to obtain a real offset value $x=(p-q)*(c-a)/(a-b)+p$, wherein:
- p is the distance between the first predetermined pattern and the third predetermined pattern;
- q is the distance between the second predetermined pattern and the third predetermined pattern;
- a is the offset value between the default position and the first image point;
- b is the offset value between the default position and the second image point; and
- c is the offset value between the default position and the third image point;

wherein said inspection process and said calculating process are performed using a computer system.

10. The method of claim 9, wherein the distance p is smaller than 20 um.

11. The method of claim 9, wherein the distance q is smaller than 20 um.

12. The method of claim 9, wherein the first predetermined pattern, the second predetermined pattern and the third predetermined pattern are disposed on a same layer of a wafer.

13. The method of claim 12, wherein the default position is disposed on another layer different the layer having the first predetermined pattern.

14. The method of claim 1, wherein the real offset value x further satisfies the relationship: $x=(p-q)*(c-b)/(a-b)+q$.

15. The method of claim 1, wherein the inspection process comprises a virtual inspection technique.

16. The method of claim 1, wherein the inspection process includes one of the group including a bright-field inspection technique, a dark-field inspection technique, and an electron beam inspection technique.

* * * * *